United States Patent
Johnson

[11] Patent Number: 6,139,583
[45] Date of Patent: Oct. 31, 2000

[54] FEMORAL PROSTHESIS

[76] Inventor: Lanny L. Johnson, 2950 E. Mount Hope Rd., Okemos, Mich. 48864

[21] Appl. No.: 09/096,611

[22] Filed: Jun. 12, 1998

[51] Int. Cl.$^7$ .................................................... A61F 2/36
[52] U.S. Cl. ................................................................ 623/23
[58] Field of Search .................................. 623/23, 22, 19

[56] References Cited

U.S. PATENT DOCUMENTS 4,750,905   6/1988   Koeneman et al. ...................... 623/23

FOREIGN PATENT DOCUMENTS 0 528 284 A1   2/1993   European Pat. Off. .................. 623/23
94/08534       4/1994   WIPO ....................................... 623/23

*Primary Examiner*—David H. Willse
*Attorney, Agent, or Firm*—Pillsbury Madison & Sutro LLP

[57] ABSTRACT

A femoral prosthesis includes a stem tapered from its proximal end to its distal end, the stem having a substantially oval-shaped cross-section along its length. The stem has a twisted waist portion intermediate its ends whereby the major axes of the cross-section on opposite sides of the waist portion are disposed at an angle of approximately 90° with respect to one another so as to conform with the geometry of an intramedullary canal within which the stem is to be received.

3 Claims, 5 Drawing Sheets

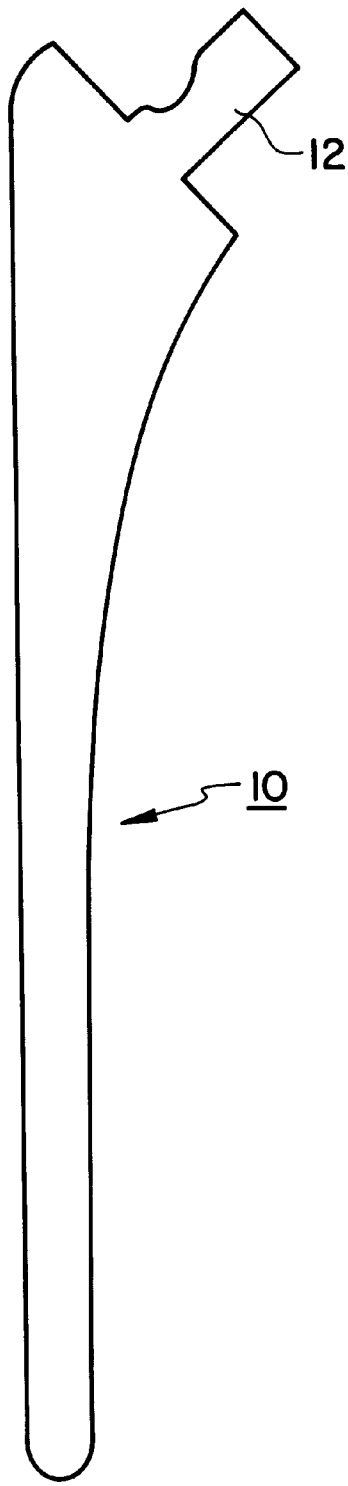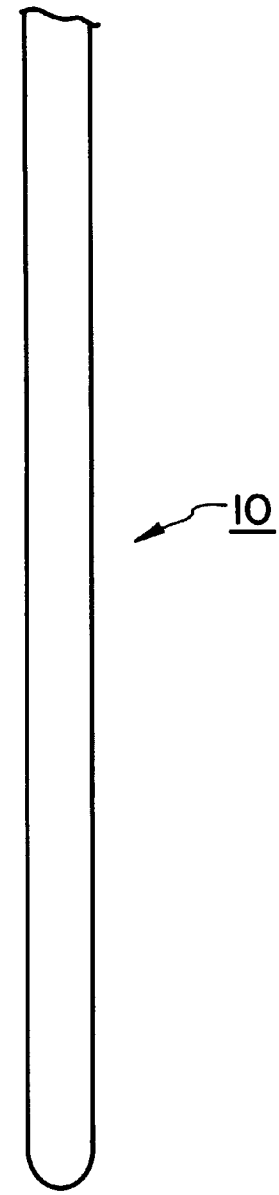
FIG. 1
(PRIOR ART)
FIG. 2
(PRIOR ART)

FEMORAL PROSTHESIS

BACKGROUND OF THE INVENTION

1. Field of the Invention

The present invention relates to a femoral prosthesis, and more particularly, to a prosthesis design which provides an improved fit within the intramedullary canal of the femur.

2. Prior Art

It is well known that the shape of the femoral intramedullary canal is variable. Thus, when a prosthesis is implanted within the canal, it must be properly fitted. If the prosthesis bears on a particular area of cortical bone surrounding the canal, pain may be experienced by the recipient of the prosthesis. Additionally, the prosthesis may loosen as a result of rotation within canal or because of downward pressure resulting from the weight of the user.

The geometry of the femoral intramedullary canal is that it has an oval shape in its upper portion adjacent the location where the femoral head and neck have been removed. The major axis of the oval extends in the medial to lateral direction. However, approximately 4 to 6 inches below its upper end, the canal narrows, and it transitions to a configuration in which it is oval shaped, the oval's major axis extending in the anterior/posterior direction.

Conventional femoral prostheses neglect the geometrical characteristics of the intramedullary canal just described. More particularly, while they are configured to accommodate the canal's proximal geometry, they typically have distal portions which are circular in cross-section. Thus, proper fitting of such prostheses is achieved only at the proximal end of the canal. This results in less than complete stable fixation leading to the problems previously described.

SUMMARY OF THE INVENTION

The present invention overcomes the shortcomings of prior art femoral prostheses by providing a femoral stem which has a substantially oval configuration over its entire length, the stem being provided with a twisted waist intermediate its ends whereby the major axis of the oval transitions by approximately 90°. This permits an implanted prosthesis to approximate the geometry of the intramedullary canal within which it is received.

DESCRIPTION OF THE DRAWINGS

The invention will be described in greater detail with respect to the accompanying drawings wherein:

FIG. 1 is a side elevational view the femoral stem of a conventional prosthesis;

FIG. 2 is an end elevational view of a portion of the femoral stem shown in FIG. 1;

DETAILED DESCRIPTION OF A PREFERRED EMBODIMENT OF THE INVENTION

Referring to FIGS. 1 and 2, a conventional femoral stem 10 is illustrated. The stem at its proximal end is provided with a neck 12 for receiving a head (not shown). As can be appreciated from FIGS. 1 and 2, the proximal portion of the stem below neck 12 has an oval cross-section. Substantially midway along its length the cross-section of the stem transitions to one which is substantially circular, and the cross-section so remains to the distal end of the stem.

Figure 3:
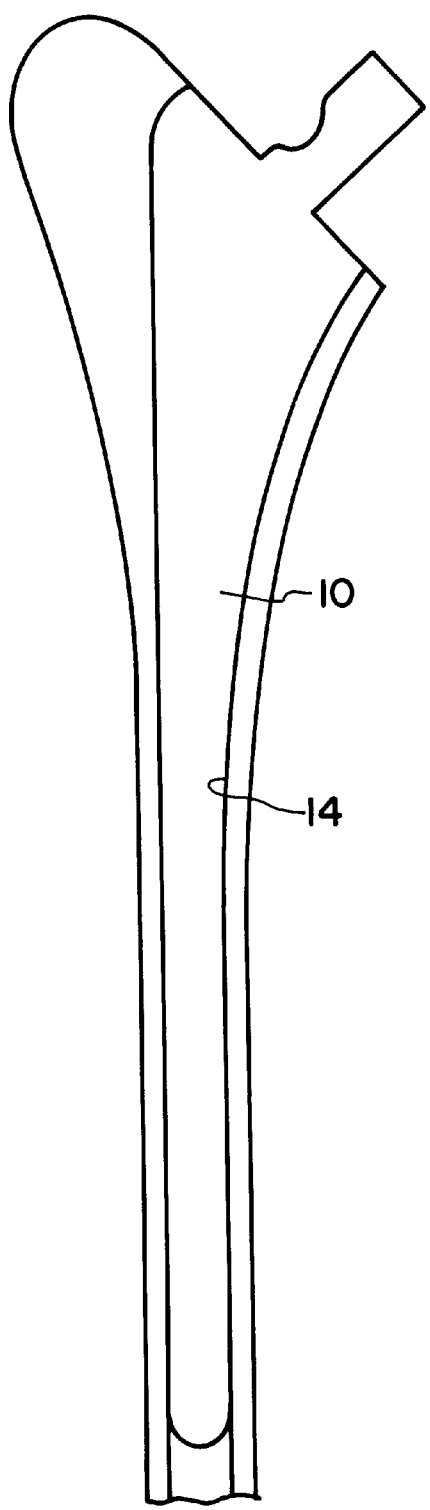
FIGS. 3 and 4 illustrate the femoral stem of FIG. 1 as it is received within a femoral intramedullary canal.
Figure 4:
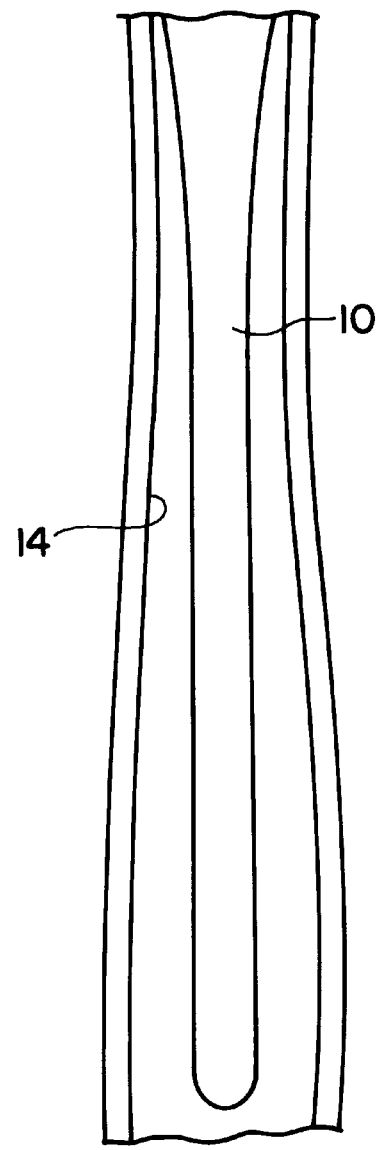

FIGS. 3 and 4 illustrate the positioning of the stem 10 within the intramedullary canal 14 of a femur 16. FIG. 3 presents a medial/lateral view of the canal, while FIG. 4 shows the canal in a anterior/posterior sense.

As can be appreciated from FIGS. 3 and 4, the stem 10 provides a fit with canal 14 which is stable in the medial to lateral direction at both the proximal and distal ends of the stem. However, because the distal end of stem 10 is substantially circular in cross-section, a very loose fit exists between the stem's distal end and the wall of the canal in the anterior/posterior direction. This significant spacing provides an opportunity for the prosthesis to loosen.

Figure 5:
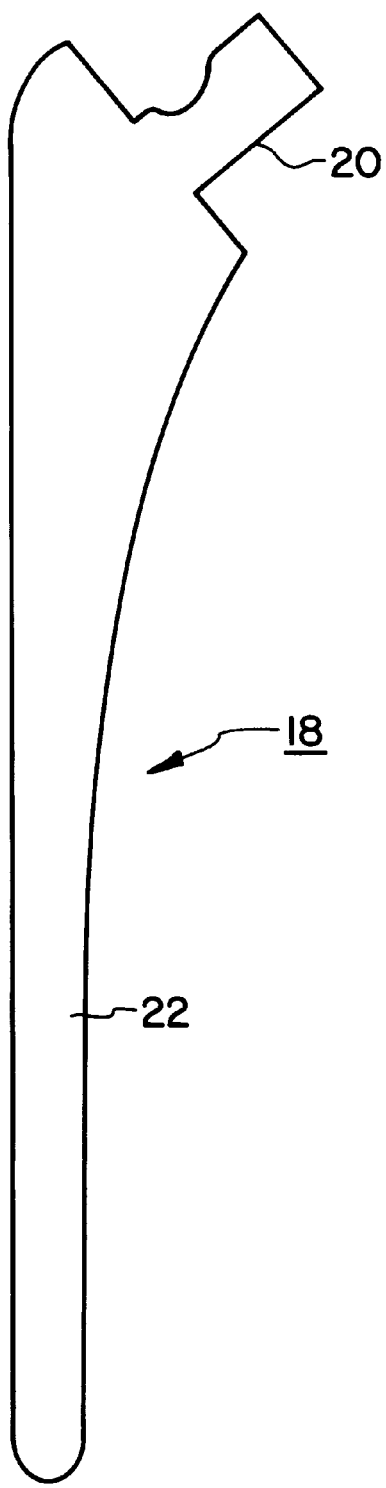
FIG. 5 is a side elevational view of the femoral stem of a prosthesis according to the present invention.
Figure 6:
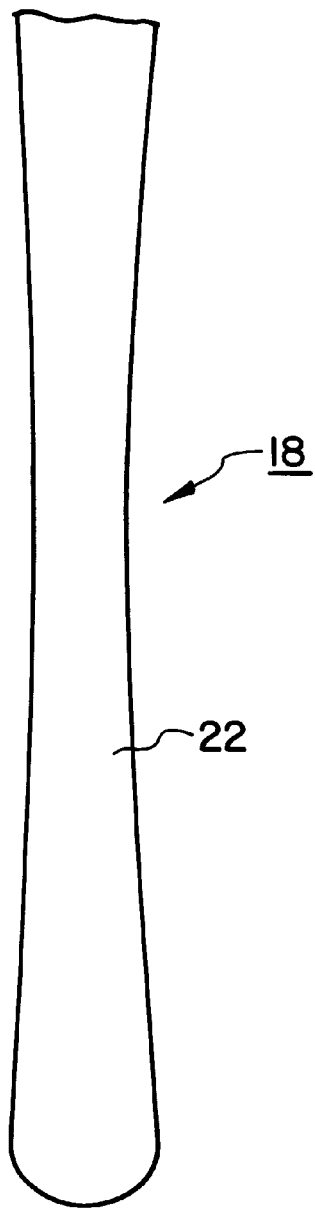
FIG. 6 is an end elevational view of a portion of the femoral stem shown in FIG. 6.

FIGS. 5 and 6 illustrate a femoral stem 18 according to the invention wherein below a neck 20, the stem is tapered towards its distal end. The cross-section of the stem 18 is oval shaped. At its proximal portion, the major axis of the cross-section extends in the medial/lateral direction (FIG. 5). However, substantially midway along the length of the stem, a twisted waist 22 is provided which transitions of stem's oval-shaped cross-section by approximately 90° to one in which the major axis of the oval at the stem's distal end extends in the anterior/posterior direction (FIG. 6).

Figure 7:
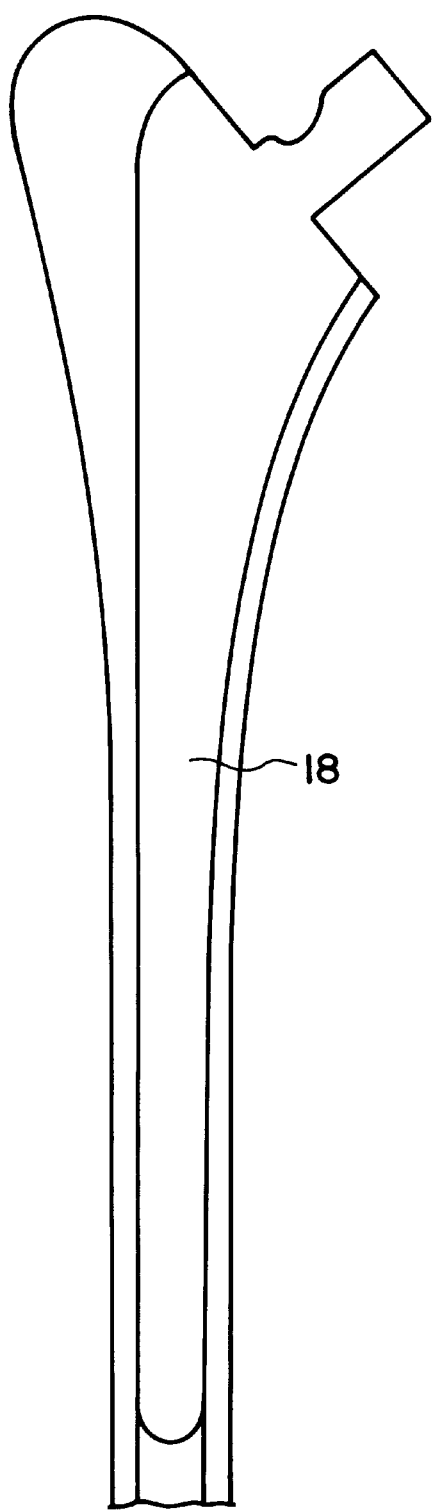
FIGS. 7 and 8 illustrate the femoral stem of FIG. 5 as it is received within a femoral intramedullary canal.
Figure 8:
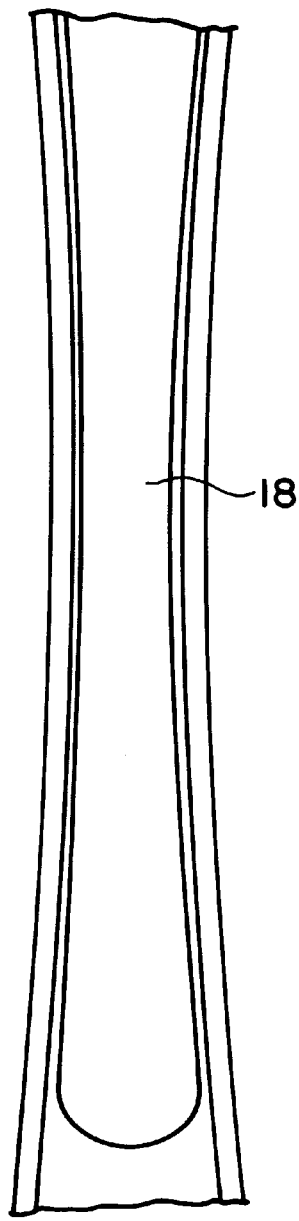

As can be appreciated from FIGS. 7 and 8, with stem 18 inserted within the intramedullary canal, a close fits is achieved between the stem and the canal's wall along the entire length of the stem. As a result, the likelihood that the stem will loosen within the canal is greatly diminished.

To ascertain the dimensions of a recipient's intramedullary canal, conventional pre-operative measurement in the form of x-rays may be employed. Additionally, the internal dimensions can be measured utilizing the instrument disclosed in applicant's U.S. Pat. No. 5,897,560, dated Apr. 27, 1999. That instrument comprises a rod having fins fixed at its distal end. The rod is inserted within the intramedullary canal until the fins contact the cortical bone which defines the wall of the canal. As a result, a central bore is formed in the canal, and the fins permit a measurement of the size of the canal at the depth at which the fins engage the wall. By using a series of such instruments having different sizes, the dimensions of the canal can be plotted.

After determining the canal's configuration and size, a series of smooth broaches having the same geometry as the femoral stem, but of successively larger sizes, are inserted into the intramedullary canal. In order to pass through the portion of the canal at which it transitions from being oval-shaped in the medial/lateral direction to the anterior/posterior direction, the broaches require their being twisted when their distal ends reach the transition area of the canal.

As broaches of increasingly greater size are inserted within the canal, the cancellous bone within the distal portion of the canal is compacted to increase its density. This form of compaction by the use of a series of broaches is disclosed in U.S. Pat. No. 5,899,907 dated May 4, 1999. The compacted bone provides a dense bed against which the distal end of the femoral stem rests when the stem subsequently is inserted into the canal in the same way described with respect to the broaches. The compacted bed provides further resistance against loosening of the prosthesis.

Figure 9:
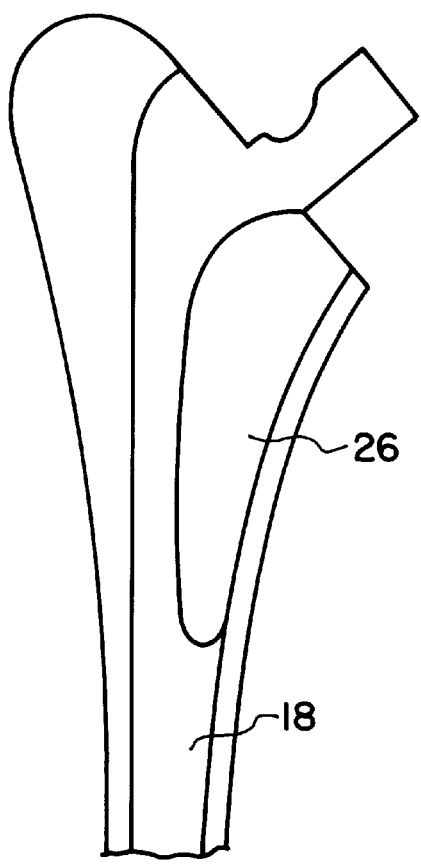
FIGS. 9 and 10 diagrammatically illustrate the displacement of cancellous bone as the femoral stem is inserted within an intramedullary canal.
Figure 10:
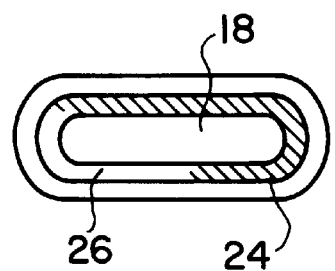

During preparation of the canal and insertion of the femoral stem, the twisting of the broaches and the stem causes displacement of cancellous bone in the proximal portion of the canal. More particularly, and as illustrated in FIGS. 9 and 10, the fact that upper end of the canal is open results in some of the cancellous bone 24 being compacted within the canal's proximal end (FIG. 10). However, a void 26 also is created (FIGS. 9 and 10), and this requires that cancellous bone harvested when the recipient's natural femoral head was removed be deposited in the void and compacted after the femoral stem is in place. This results in a tight bone mass which firmly supports the stem's proximal portion.

Although not specifically disclosed in applicant's U.S. Pat. No. 5,897,560, the bore-forming and measuring device for the intramedullary canal can include a tube so as to permit suction of the bone marrow to remove fat and decompress pressure in the canal as the bore is formed.

The prosthesis which has been described permits a very close fit along its entire length with the wall of the intramedullary canal. While the invention contemplates the use of a metal femoral stem because the space between the stem and the canal's wall is filled with compacted bone, it becomes possible to use a stem made from biodegradable material to achieve a true anatomic result.

Although the femoral stem illustrated contains a neck to which the head portion of the prosthesis can be attached, it will be understood that the stem may have a one piece neck and head.

It further will be understood that the prosthesis described, and the broaches used to prepare the site for insertion of the femoral stem, dictate that they are usable on only one side of the body. Thus, separate sets for left and right side applications are required.

What is claimed is:

1. A femoral prosthesis, comprising:

a femoral stem tapered from a proximal end to a distal end thereof, said stem having a substantially oval-shaped cross-section along its length except for a waist portion located substantially midway between the proximal and distal ends of the prosthesis, said waist portion including a twist of substantially 90° whereby major axes of oval cross-sections an opposite sides of the waist portion are disposed at an angle of substantially 90° with respect to one another.

2. A femoral prosthesis according to claim 1, wherein said stem is formed of metal.

3. A femoral prosthesis according to claim 1, wherein said stem is formed of a biodegradable material.

* * * * *